United States Patent
Barberá-Guillem

(12) 
(10) Patent No.: US 6,252,664 B1
(45) Date of Patent: Jun. 26, 2001

(54) FLUORESCENCE FILTER CUBE FOR FLUORESCENCE DETECTION AND IMAGING

(75) Inventor: Emilio Barberá-Guillem, Powell, OH (US)

(73) Assignee: BioCrystal Ltd., Westerville, OH (US)

( * ) Notice: Subject to any disclaimer, the term of this patent is extended or adjusted under 35 U.S.C. 154(b) by 0 days.

(21) Appl. No.: 09/419,134

(22) Filed: Oct. 15, 1999

(51) Int. Cl.$^7$ .............................. G01N 21/64; G02B 27/14
(52) U.S. Cl. .................. 356/417; 250/461.1; 359/634
(58) Field of Search .................... 356/317, 318, 356/417, 385, 389, 634; 250/458.1, 459.1, 461.1, 461.2

(56) References Cited

U.S. PATENT DOCUMENTS 5,880,473 * 3/1999 Ginestet ........................... 250/458.1
5,943,129 * 8/1999 Hoyt et al. ........................ 356/318

OTHER PUBLICATIONS

Instruction manual entitled "Instructions, BX–FLA, reflected light fluorescence attachment", published by Olympus, (undated).

* cited by examiner

*Primary Examiner*—F. L. Evans
(74) *Attorney, Agent, or Firm*—M. Bud Nelson

(57) ABSTRACT

A fluorescence cube comprising a housing; an exciter filter which allows passage of an incident light comprising a spectral range of from about 200 nanometers to about 400 nanometers; and either a beam splitter or a dichroic mirror which directs the incident light in a desired direction, and which transmits an emitted light in a desired direction. Also disclosed is a method of using the fluorescence cube for acquiring multicolor fluorescence images, the method comprising fluorescence labeling of a substrate with more than one species of water-soluble nanocrystals; and imaging the labeled substrate with a detection system comprising the fluorescence cube by exposing the labeled substrate to an incident light comprising an excitation spectral range, and detecting a transmitted light comprising an emission spectral range.

30 Claims, 6 Drawing Sheets

FLUORESCENCE FILTER CUBE FOR FLUORESCENCE DETECTION AND IMAGING

FIELD OF INVENTION

This invention relates to an optic system to provide true color fluorescence images of fluorescently labeled substrates; and more particularly, to a fluorescence filter cube that can be used to detect a wide variety of colors simultaneously, such as in multicolor fluorescence labeling.

BACKGROUND OF THE INVENTION

Detection or detection and imaging of molecules and/or biological processes is an area of scientific and medical importance which is in constant need for innovation. Visual imaging is of particular value to the medical imaging industry and to the pharmaceutical industry. In medical imaging, there is a demand for new imaging agents (contrast agents or diagnostic agents) that enhance the assessment of one or more of healthy tissue, a disease process affecting tissue, and a disease state of affected tissue. As to the pharmaceutical industry, in drug development it is particuarly important to monitor one or more of: (a) the distribuion of the drug in a particular target organ or tissue; (b) the interaction of the drug within the organ or tissue; (c) internalization of the drug by tissue cells, when the target of action is intracellular; and (d) metabolism or bioclearance of the drug in living tissues.

Typically, conventional fluorescent labels (e.g., fluorescein, rhodamine, phycoerythrin, an the like) are used for fluorescence detection and/or imaging. These conventional fluorescent labels typically have an excitation spectrum that may be quite narrow; and hence it is often difficult to find a wavelength spectrum of light suitable for simultaneously exciting several different fluorescent labels (e.g., differing in color of fluorescence emission). However, even when a single light source is used to provide a excitation wavelength spectrum (in view of the spectral line width), often there is insufficient spectral spacing between the emission optima of different species (e.g., differing in color) of fluorescent labels to permit individual and quantitative detection without substantial spectral overlap. Thus, when using a combination of different fluorescent labels, multiple filters are typically needed to detect the resultant emission spectra of the combination. For example, for fluorescent detection of a substrate labeled with fluoroscein isothiocyanate (FITC), a filter cube comprising a FITC dichromic filter set is used (excitation at 450–490 nm, and peak emission at 520 nm). This example illustrates the current state of the art of fluorescence filter cubes ("fluorescence cubes"). That is, a fluorescence cube is typically designed to ensure that the substrate is excited by a desired short wavelength (specific for the specie of fluorescent label sought to be detected), and detection of wavelengths in a limited spectral band. Table 1 further illustrates the current state of the art of conventional fluorescence cubes comprised of a dichroic mirror (shown is emission wavelength cutoff; i.e., less than the emission wavelength cutoff is reflected away, greater than emission wavelength cutoff is passed onto the barrier filter), an exciter filter (shown is spectrum of incident light), a barrier filter (shown is wavelength cutoff; i.e., less than wavelength cutoff is blocked, greater than wavelength cutoff is passed onto the detector), and fluorochrome detected by the fluorescence cube.

TABLE 1

| Dichroic mirror | Exciter filter | Barrier filter | Fluorochrome |
| --- | --- | --- | --- |
| 400 nm | 330 nm–385 nm | 420 nm | DAPI, Hoechst 33342 |
| 455 nm | 400 nm–410 nm | 455 nm | Catecholamine, Serotonin |
| 455 nm | 400 nm–440 nm | 475 nm | Quinacrine |
| 455 nm | 420 nm–440 nm | 475 nm | Acriflavine, Thioflavin S |
| 500 nm | 450 nm–480 nm | 515 nm | FITC |
| 500 nm | 470 nm–490 nm | 515 nm | Acridine orange |
| 570 nm | 510 nm–550 nm | 590 nm | Rhodamine, Propidium iodide, TRITC |
| 600 nm | 545 nm–580 nm | 610 nm | Texas red |

Current techniques for acquiring multicolor fluorescence images, using a filter-based imaging method to measure the fluorescence from a substrate labeled with multiple fluorescent labels, are both time-consuming and complicated. Typically, no more than 3 different fluorescent labels may be used due to limitations related to different excitation spectra and different emission spectra. Multicolor fluorescence images are then acquired, one image for each fluorescent label used, by rotating a filter wheel into place. The filter wheel has various filters, wherein each filter or a filter combination is used for a specific fluorescent label (See, e.g., Table 1). Additionally, it is often necessary to make adjustments for each peak wavelength spectrum (i.e., for each label used) such as readjusting the focus of the image, and/or selecting an optimal exposure time for each peak emission spectrum when using a detection system that includes a charge coupling device (CCD) camera. A series of monochrome images are generated, each image corresponding to the peak emission spectrum of a specific fluorescent label. These images are false-colored and then superimposed onto one image using a computer.

Recently, a new class of fluorescent labels have been, and continued to be, developed for use in biological, biomedical, and biochemical applications. These fluorescent labels comprise water-soluble semiconductor nanocrystals ("quantum dots"). "Water-soluble" is used herein to mean sufficiently soluble or suspendable in a aqueous-based solution, such as in water or water-based solutions or physiological solutions, including those used in the various fluorescence detection systems as known by those skilled in the art. Generally, quantum dots can be prepared which result in relative monodispersity; e.g., the diameter of the core varying approximately less than 10% between quantum dots in the preparation. Examples of quantum dots are known in the art to have a core selected from the group consisting of CdSe, CdS, and CdTe (collectively referred to as "CdX"). CdX quantum dots have been passivated with an inorganic coating ("shell") uniformly deposited thereon. Passivating the surface of the core quantum dot can result in an increase in the quantum yield of the fluorescence emission, depending on the nature of the inorganic coating. The shell which is used to passivate the quantum dot is preferably comprised of YZ wherein Y is Cd or Zn, and Z is S, or Se. Typically, CdX core/YZ shell quantum dots are overcoated with trialkylphosphine oxide, with the alkyl groups most commonly used being butyl and octyl. One method to make the CdX core/YZ shell quantum dots water-soluble is to exchange this overcoating layer with a coating which will make the quantum dots water-soluble. For example, a mercaptocarboxylic acid may be used to exchange with the trialkylphosphine oxide coat. Exchange of the coating group is accomplished by treating the water-insoluble quantum dots with a large excess of neat mercaptocarboxylic acid. Alternatively, exchange of the coating group is accomplished by treating the water-insoluble quantum dots with a large excess of mercaptocarboxylic acid in $CHCl_3$ solution (Chan and Nie, 1998, *Science* 281:2016–2018). The thiol group of the new coating molecule forms Cd (or Zn)-S bonds, creating a coating which is not easily displaced in solution. Another method to make the CdX core/YZ shell quantum dots water-soluble is by the formation of a coating of silica around the dots (Bruchez, Jr. et al., 1998, *Science* 281:2013–2015). An extensively polymerized polysilane shell imparts water solubility to nanocrystalline materials, as well as allowing further chemical modifications of the silica surface. Generally, these "water-soluble" quantum dots require further functionalization to make them sufficiently stable in an aqueous solution for practical use in a fluorescence detection system (as described in more detail in U.S. Ser. No. 09/372729, the disclosure of which is herein incorporated by reference), particularly when exposed to air (oxygen) and/or light. Water-soluble functionalized nanocrystals are extremely sensitive in terms of detection, because of their fluorescent properties (e.g., including, but not limited to, high quantum efficiency, resistance to photobleaching, and stability in complex aqueous environments); and comprise a class of semiconductor nanocrystals that may be excited with a single peak wavelength of light resulting in detectable fluorescence emissions of high quantum yield and with discrete fluorescence peaks (e.g., having a narrow spectral band ranging between about 10 nm to about 60 nm).

However, there lacks an optical system comprising a single fluorescence cube which could be used for detecting, or detecting and imaging, (collectively referred to hereinafter as "acquiring") fluorescence spectra generated by a combination of different fluorescent labels used together in multicolor fluorescence analysis of a labeled substrate. More particularly, there is a need for a simple device that enables the simultaneous measurement of the emission spectrum of each of a plurality of different species (e.g., differing in emission spectrum, and hence color) of water-soluble semiconductor nanocrystals which are used in a combination to achieve multicolor fluorescence analysis.

SUMMARY OF THE INVENTION

The present invention provides a detection system for acquiring fluorescence spectra generated by a combination of different water-soluble semiconductor nanocrystals used together in multicolor fluorescence analysis of a labeled substrate. The detection system is capable of simultaneously acquiring fluorescence spectra from all pixels of a field of view, such as provided by a fluorescence microscope or other optical imaging device; and hence, can simultaneously detect in a single measurement the locations in a substrate of one or more labeled affinity ligands. Each type of affinity ligand may be labeled with one or more of a different water-soluble semiconductor nanocrystal (e.g., differing in discrete emission spectrum) than that used to label the other types of affinity ligand. Using a single fluorescence cube according to the present invention to acquire a wide range of fluorescence spectra has been found to save time, effort, and expense, that is otherwise spent on choosing optimal filters for a filter-based measurement of each emission spectrum. By enabling the simultaneous measurement of the emission spectra from a number of different water-soluble semiconductor nanocrystals, eliminated is the need for false color imaging, and the need to sequentially acquire images one emission spectrum at a time.

In one embodiment, the detection system is a reflected illumination system comprising a fluorescence cube. The fluorescence cube comprises a housing; and an exciter filter and a dichroic mirror which are operatively positioned in, and secured to, the housing. The cube may further comprise a barrier filter. However, in the detection system according to the present invention, and in addition to a housing, the cube comprises an exciter filter and dichroic mirror combination selected such that, unlike prior art cubes, multicolor fluorescence images can be acquired using a single cube, as obtained by labeling with different species of water-soluble semiconductor nanocrystals. The fluorescence cube may be used to detect any water-soluble fluorescent nanocrystals for any application in which acquiring one or more fluorescence emission spectrum is desired. However, a preferred application may be practiced to the exclusion of applications other than the preferred application.

In another embodiment, the detection system is a reflected illumination system comprising a fluorescence cube. The fluorescence cube comprises a housing, an exciter filter, a regular beam splitter, and a barrier filter. In this detection system according to the present invention, the combination comprising the exciter filter, the beam splitter, and the barrier filter is selected such that, unlike prior art cubes, multicolor fluorescence images can be acquired using a single cube, as obtained by labeling with different species of water-soluble semiconductor nanocrystals. The fluorescence cube may be used to detect any water-soluble fluorescent nanocrystals for any application in which acquiring an emission spectral range comprising one or more fluorescent emission spectrum is desired. However, a preferred application may be practiced to the exclusion of applications other than the preferred application.

The above and other objects, features, and advantages of the present invention will be apparent in the following Detailed Description of the Invention when read in conjunction with the accompanying drawings.

BRIEF DESCRIPTION OF THE DRAWINGS

FIG. 3 is a black and white photographic representation of showing cells labeled in a multicolor analysis and imaged in color using a fluorescence cube according to the present invention, wherein:

DETAILED DESCRIPTION OF THE INVENTION

Figure 1:
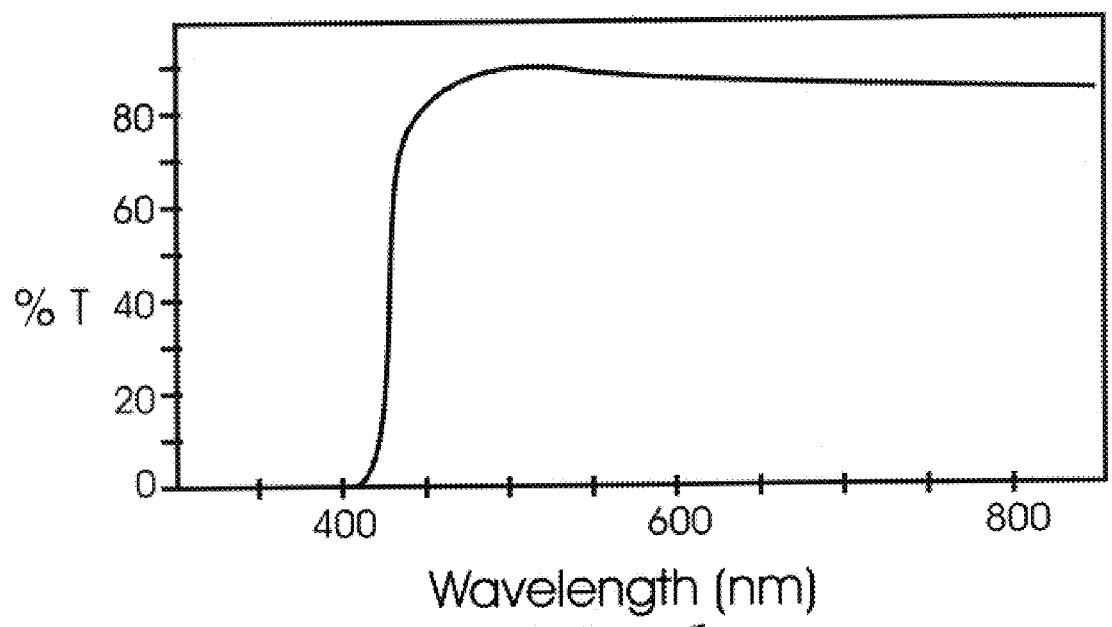
FIG. 1 is a graph illustrating the spectral range of emission,wavelengths capable of being detected with one embodiment of the fluorescence cube according to the present invention.

By the term "substrate" is meant, for the purposes of the specification to refer to a molecule of an organic nature (e.g., microorganism (bacterial, viral, etc.), tissue component, etc.) or inorganic nature (e.g., chemical), the presence and/or quantity of which is being tested for; and which contains a molecular component (domain or sequence or receptor or epitope or portion or chemical group or determinant) for which the affinity ligand has binding specificity. The nature of the substrate is not critical to the invention, as a wide variety of substrates are the subject of fluorescence analyses as known to those skilled in the art. It may be a molecule that includes, but is not limited to, a nucleic acid molecule, protein, glycoprotein, eukaryotic or prokaryotic cell, lipoprotein, peptide, carbohydrate, lipid, phospholipid, aminoglycans, chemical messenger, biological receptor, structural component, metabolic product, enzyme, antigen, drug, therapeutic, toxin, inorganic chemical, organic chemical, and the like. The substrate may be extracellular, intracellular, in vivo, in vitro, in situ, or ex vivo.

By the term "affinity ligand" is meant, for purposes of the specification, to mean a molecule which has binding specificity and avidity for a molecular component of, or associated with, a substrate. The nature of the affinity ligand is not critical to the invention, as a wide variety of affinity ligands are used as targeting molecules in fluorescence analyses as known to those skilled in the art. In general, affinity ligands are known to those skilled in the art to include, but are not limited to, lectins or fragments (or derivatives) thereof which retain binding function; monoclonal antibodies ("mAb", including chimeric or genetically modified monoclonal antibodies (e.g., "humanized"), and immunoreactive fragments of mAb as known to those skilled in the art); peptides; aptamers; nucleic acid molecules (including, but not limited to, single stranded RNA or single-stranded DNA, or single-stranded nucleic acid hybrids); avidin, or streptavidin, or avidin derivatives; a drug; and the like. The invention may be practiced using a preferred affinity ligand to the exclusion of affinity ligands other than the preferred affinity ligand.

By the term "fluorescence analysis" is meant, for purposes of the specification and claims, to mean any method known to those skilled in the art by which a substrate is fluorescently labeled, and acquired is any fluorescence emission of an excited, labeled substrate. Fluorescence labeling is achieved by using water-soluble nanocrystals having one or more affinity ligands operably linked thereto, as previously described herein. Exemplary methods may include, but are not limited to, a fluorescence-based immunoassay, fluorescence microscopy, fluorescence endoscopy (see, e.g., U.S. Pat. No. 5,891,016), flow cytometry, fluorescence in-situ hybridization, nucleic acid amplification with one or more fluorescently labeled nucleotides, nucleic acid sequencing using one or more fluorescently labeled nucleotides, fluorescence imaging, and the like. The invention may be practiced using a preferred fluorescence analysis to the exclusion of fluorescence analyses other than the preferred fluorescence analysis. Likewise, the fluorescence cube according to the present invention may be operatively coupled to an instrument used in acquiring fluorescence spectra for fluorescence analysis. As an illustrative, non-limiting example, the fluorescence cube may operatively coupled to an appropriate detection means or system which may include, but is not limited to, one or more of: one or more photodetectors, a filter, a CCD camera, a fluorescence microscope, an endoscopic imaging system, an endoscopic fluorescence imaging microscope, a fiber optic fluorescence imaging microscope, a computer used in the fluorescence analysis, and the like.

By the term "spectral range" is meant, for purposes of the specification and claims, to mean a wavelength range comprising a "low wavelength value" wherein light of less than the low wavelength value is blocked or reflected or otherwise excluded; and a "high wavelength value" wherein light of greater than this high wavelength value is blocked or reflected or otherwise excluded, as will be more apparent from the following descriptions.

Generally, each species of water-soluble fluorescent nanocrystals can be excited, by exposure to an appropriate excitation spectrum, to emit an emission spectrum and fluorescence peak in the spectral range of about 400 nm to about 750 nm. As known to those skilled in the art of nanocrystals, the absorbance peak and fluorescence peak emission depend on properties of the nanocrystals which may include, but are not limited to, the chemical nature, doping agent (if any), and core size. The following are illustrative examples of altering the size of the nanocrystal to achieve various colors. Water-soluble CdSe/ZnS nanocrystals having a substantially uniform size comprising a diameter of about 68.4 angstroms (Å) may be excited with light in the spectral range of from about 300 nm to about 400 nm, and emit a fluorescence peak (orange) at 609 nm which may be detected using appropriate detection means. Water-soluble CdSe/ZnS nanocrystals having a substantially uniform size comprising a diameter of about 53.2 Å may be excited with light of a spectral range of from about 300 nm to about 400 nm, and emit a fluorescence peak (yellow) at 545 nm which may be detected using appropriate detection means. Water-soluble CdSe/ZnS nanocrystals having a substantially uniform size comprising a diameter of about 46.6 Å may be excited with light of a spectral range of from about 300 nm to about 400 nm, and emit a fluorescence peak (green) at 522 nm which may be detected using appropriate detection means. Water-soluble CdSe/ZnS nanocrystals having a substantially uniform size comprising a diameter of about 23 Å may be excited with light of a spectral range of from about 300 nm to about 400 nm, and emit a fluorescence peak (blue) at 480 nm which may be detected using appropriate detection means.

Figure 4:
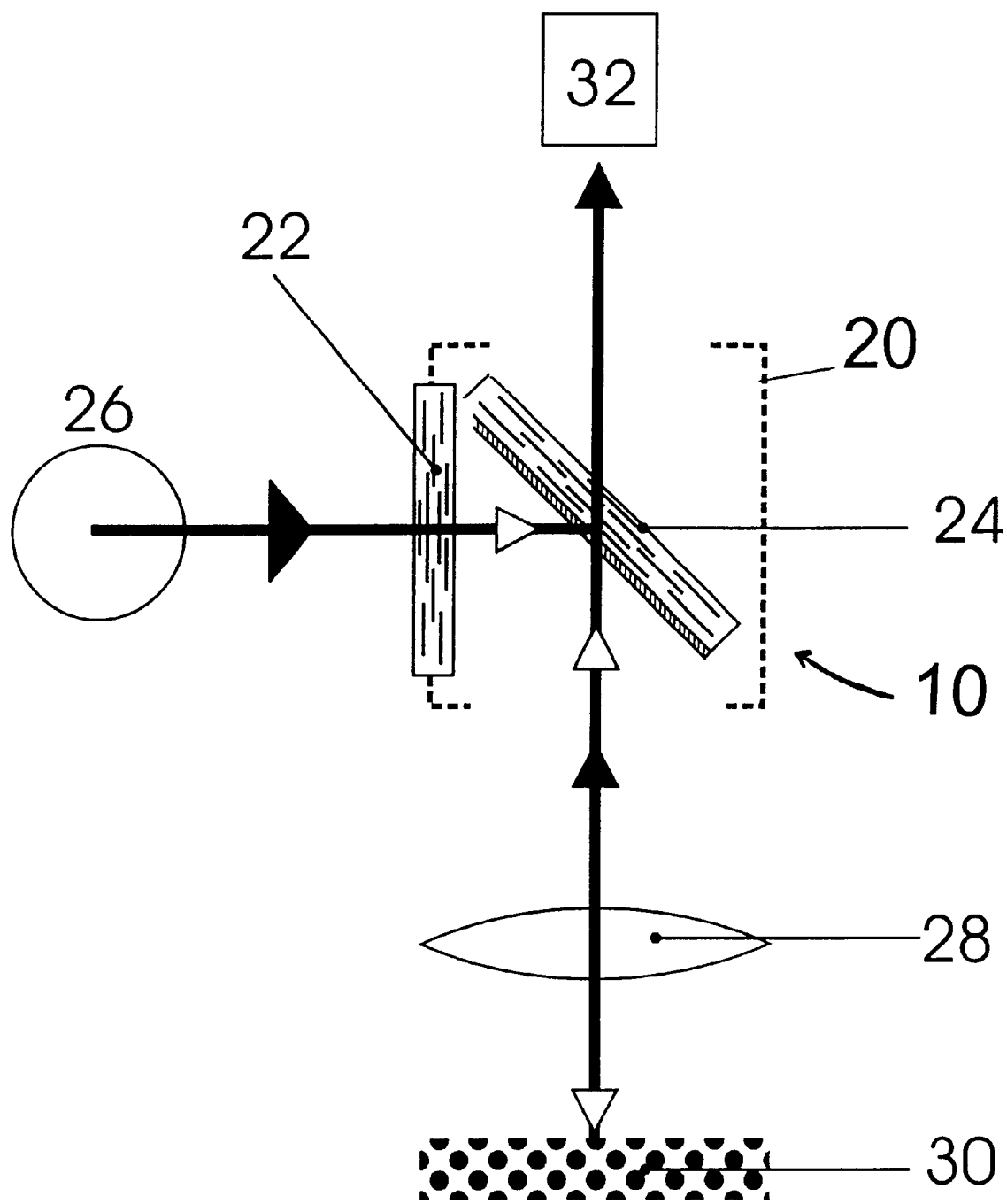
FIG. 4 is a schematic illustration of one embodiment of the fluorescent cube according to the present invention.

The fluorescence cube of the present invention was designed for acquiring fluorescence emission(s) associated with use of water-soluble nanocrystals to ensure that the nanocrystals are excited by an excitation light source of a desired wavelength spectral range, and that fluorescence emission comprising a wavelength spectral range for each representative color used in the analysis can be transmitted to an appropriate detector means. As illustrated in FIG. 4, in one embodiment, fluorescence cube 10 comprises a housing 20, an exciter filter 22, and a dichroic mirror 24. A light source 26 is illuminated through an opening in housing 20 to exciter filter 22, wherein exciter filter 22 allows only light of certain wavelength(s) to pass through ("incident light"). In a preferred embodiment, the incident light from the exciter filter comprises a spectral range of from about 200 nm to about 400 nm; and in a more preferred embodiment, the incident light from the exciter filter comprises a spectral range of from about 310 nm to about 400 nm with a maximum transmission peak of from about 360 nm to about 365 nm; and in another preferred embodiment, the incident light from the exciter filter comprises a spectral range of from about 355 nm to about 375 nm with a maximum transmission peak at about 365 nm.

In continuing with this illustrative example, the incident light from exciter filter 22 reaches dichroic mirror 24. In a preferred arrangement, the dichroic mirror is operatively positioned at an angle of 45° with respect to the optical axis of the incident light from the exciter filter, thereby reflecting the light comprising the excitation spectral range in a desired direction; e.g., through an opening in housing 20, towards objective 28, and to a sample comprising substrate 30. If the substrate is labeled with the water-soluble nanocrystals used in the fluorescence analysis, exposing the nanocrystals to an excitation light will cause the nanocrystals to become excited and emit an emission spectral range that is dependent on the species of water-soluble nanocrystals used to label the substrate. For example, where a plurality of species (e.g., differing in size) of water soluble nanocrystals is used to perform multicolor fluorescence analysis, the emitted light will comprise emitted fluorescence spectra of a plurality of discrete fluorescence peaks in a spectral range of about 420 nm to about 750 nm, dependent upon the species of functionalized nanocrystals used. Thus, light emitted from sample 30 then reaches dichroic mirror 24; e.g., is passed back up through objective 28 and an opening in housing 20 to dichroic mirror 24. The dichroic mirror may be chosen to reflect in a direction away from detector means 32 substantially all unwanted wavelengths of light emitted from the sample, and transmits (e.g., reflects) emitted light comprising a selected spectral range in a desired direction; e.g., directs passage of the emitted light of a selected spectral range through an opening in the housing and to detector means 32. In one preferred embodiment, and as shown in FIG. 1, the dichroic mirror transmits to the detector means an emitted light in the spectral range comprising from about 415 nm to about 800 nm. Thus, in this preferred embodiment, reflected away is any emitted light comprising wavelengths less than about 415 nm and light comprising wavelengths greater than about 800 nm; and transmitted to the detector means is emitted light of a spectral range between about 415 nm and about 800 nm. In another preferred embodiment, the dichroic mirror transmits to the detector means an emitted light in the spectral range comprising from about 415 nm to about 750 nm. In both of these preferred embodiments, the dichroic mirror is chosen so as to enable transmission of emitted fluorescence in a spectral range that corresponds to colors ranging from blue to green to yellow to orange to red, as found in the visible spectrum. The emission spectral range that is transmitted may also correspond to variations of these primary colors (e.g., a green-yellow).

Figure 5:
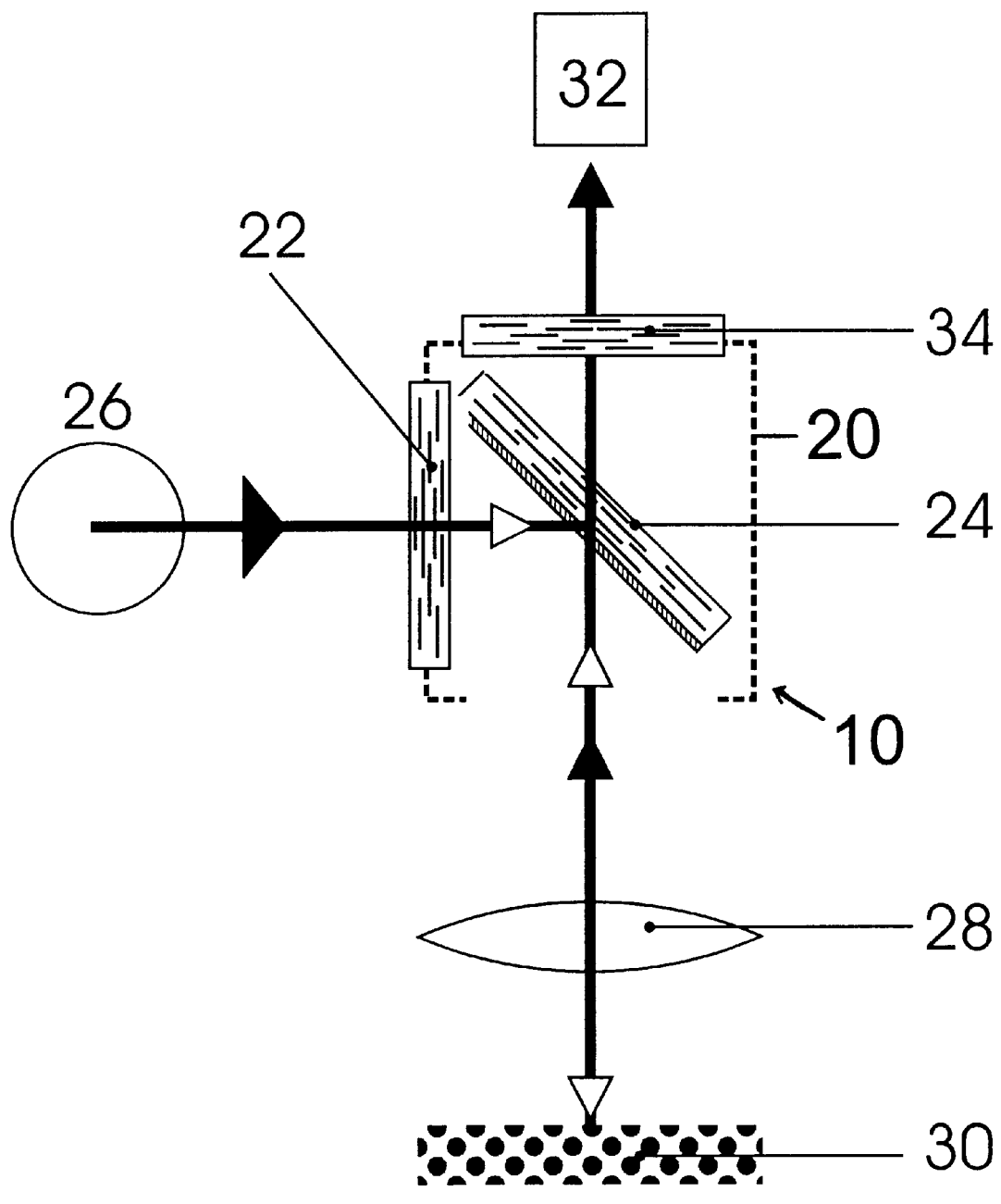
FIG. 5 is a schematic illustration of another embodiment of the fluorescent cube according to the present invention.

The fluorescence cube may further comprise a barrier filter, operatively positioned between the dichroic mirror and the detector means, to ensure that blocked out from reaching the detector means is any light that may be undesirable or harmful (e.g., wavelengths of light of a spectral range of less than 400). For example, where the detector means comprises an eyepiece of a fluorescence microscope, wavelengths of less than 400 nm that reach the eyepiece may be harmful to the eyes of the viewer. Accordingly, in instances in which the dichroic mirror does not function to reflect away from the detector means all of such unwanted wavelengths of light emitted from the sample, the barrier filter may function to block out such unwanted wavelengths before the transmitted light reaches the detector means. Thus, the fluorescence cube according to the present invention, as illustrated in FIG. 5, may further comprise a barrier filter 34, operatively positioned between dichroic mirror 24 and detector means 32, which may eliminate undesirable light from reaching detector means 32. The undesirable light emitted from the sample may comprise background fluorescence. Sources of background fluorescence include, but are not limited to, auto-fluorescence of the sample comprising the substrate, and unwanted fluorescence resulting from selection of an inappropriate or sub-optimal (e.g., quality or property or positioning of) dichroic mirror and/or exciter filter. In a preferred embodiment of the present invention, the barrier filter blocks out light of less than about 400 nm from reaching the detector means; and in another preferred embodiment, the barrier filter blocks out light of less than about 420 nm from reaching the detector means.

In another embodiment, the fluorescence cube comprises a housing, an exciter filter and a dichroic mirror. Preferably, the incident light from the exciter filter comprises a spectral range of from about 200 nm to about 400 nm. Also preferable, the incident light from the exciter filter comprises a spectral range of from about 310 nm to about 400 nm with a maximum transmission peak of from about 360 nm to about 365 nm. Also preferably, the incident light from the exciter filter comprises a spectral range of from about 355 nm to about 375 nm with a maximum transmission peak at about 365 nm. In a preferred arrangement, the dichroic mirror is operatively positioned at an angle of 45° with respect to the optical axis of the incident light, thereby reflecting the incident light comprising the excitation spectral range in a desired direction; e.g., through an opening in the housing and towards an objective and through to a sample comprising the substrate. The excitation light will then cause the nanocrystals, when present with the substrate, to become excited and emit an emission spectral range that is dependent on the species of water-soluble nanocrystals used to label the substrate. The dichroic mirror may be chosen to reflect in a direction away from the detector means substantially all unwanted wave-lengths of light emitted from the sample, and transmit to the detector means an emitted light comprising a selected emission spectral range. In this illustrative embodiment, the dichroic mirror is selected and operatively positioned to transmit emitted light to the detector means comprising only a portion of the spectral range of from about 415 nm to about 800 nm. For example, the dichroic mirror may be chosen to transmit emitted light in the spectral range of from about 415 nm to about 550 nm, which would correspond to detection of colors ranging from blue to green to yellow in a multicolor fluorescence analysis. In another example, the dichroic mirror may be chosen to transmit emitted light in the spectral range of from about 530 nm to about 750 nm, which would correspond to detection of colors ranging from yellow to orange to red in a multicolor fluorescence analysis. The dichroic mirror may be chosen to transmit other spectral ranges of emitted light comprising a portion of the range of from about 415 nm to about 800 nm, as will be apparent to those skilled in the art based on the descriptions herein. The invention may be practiced using a dichroic mirror that transmits a preferred spectral range comprising a portion (ranging over a spectral band of about 100 nm or greater) of the range of from about 415 nm to about 800 nm to the exclusion of spectral ranges other than the preferred spectral range. The fluorescence cube according to this embodiment may further comprise a barrier filter operatively positioned between the dichroic mirror and the detector means. Preferably, the barrier filter blocks out light of less than about 400 nm from reaching the detector means; and also preferred, the barrier filter blocks out light of less than about 420 nm from reaching the detector means.

Figure 6:
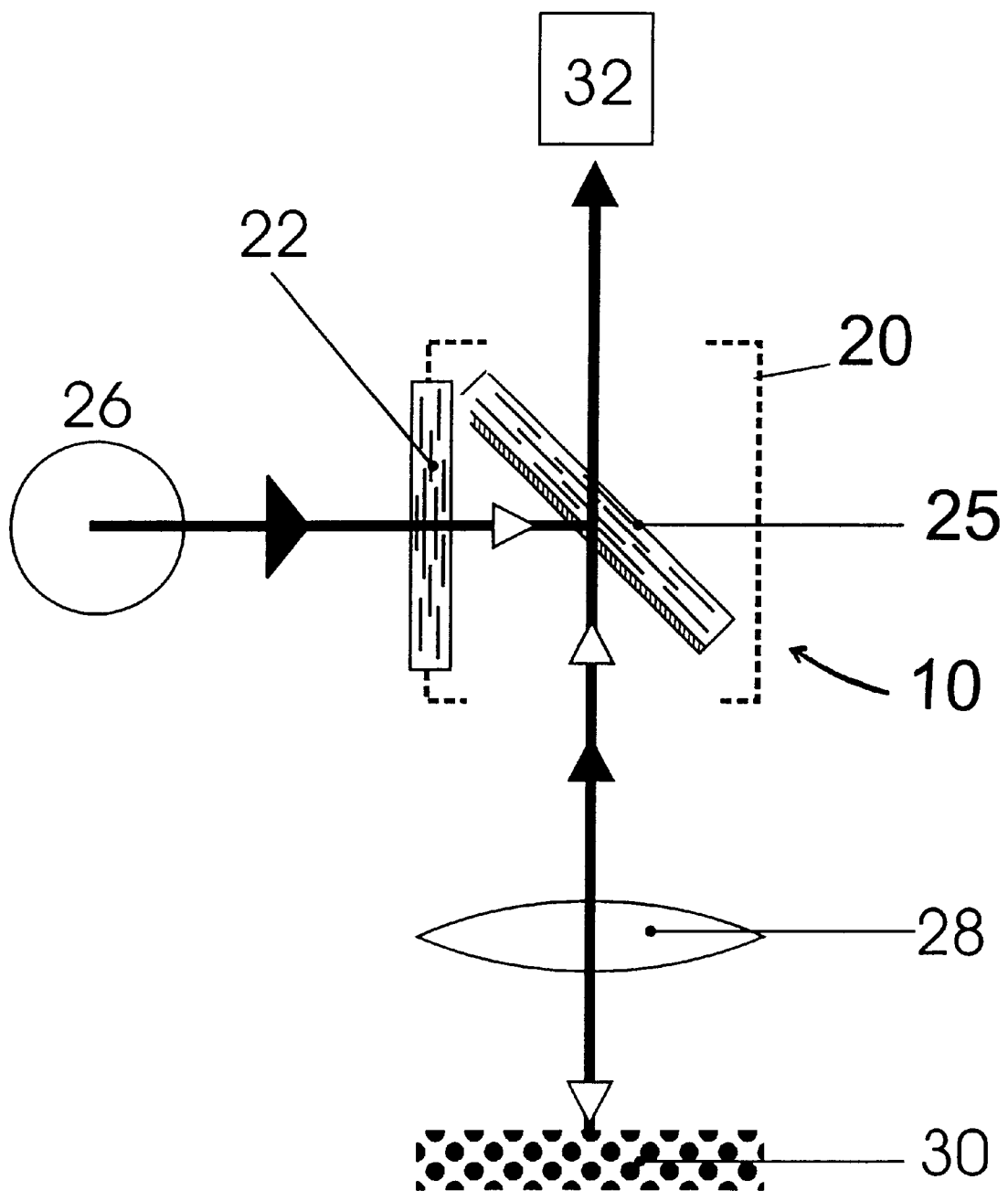
FIG. 6 is a schematic illustration of another embodiment of the fluorescent cube according to the present invention.
Figure 7:
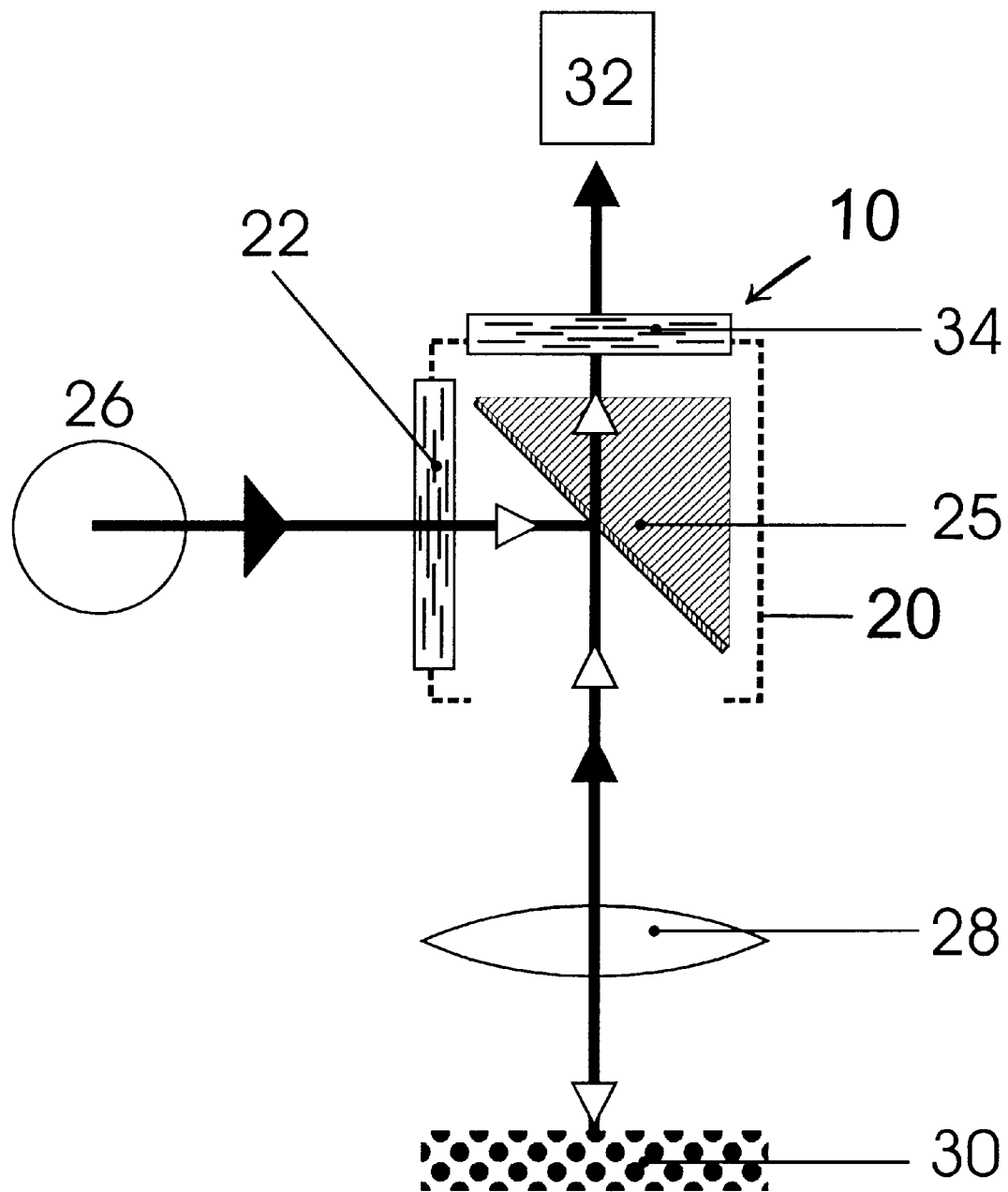
FIG. 7 s a schematic illustration of another embodiment of the fluorescent cube according to the present invention.

In another embodiment, as illustrated in FIGS. 6 & 7, fluorescence cube 10 comprises a housing 20, an exciter filter 22 and a beam splitter 25. Preferably, the incident light from the exciter filter comprises an excitation spectral range of from about 200 nm to about 400 nm. Also preferable, the incident light from the exciter filter comprises a spectral range of from about 310 nm to about 400 nm with a maximum transmission peak at about 360 nm to about 365 nm. Also preferably, the incident light from the exciter filter comprises a spectral range of from about 355 nm to about 375 nm with a maximum trans-mission peak at about 365 nm. The beam splitter is chosen and operatively positioned to direct various beams of light provided thereto to different paths. Thus, any type of beam splitter including a prism type (see, FIG. 7), a plate type (see, FIG. 6), and the like may be used as long as they function as beam splitters. Thus, one function of the beam splitter is to direct a proportion of the incident light comprising an excitation spectral range in a desired direction; e.g., through an opening in the housing and towards an objective and through to a sample comprising the substrate. The excitation light will then cause the nanocrystals, when present with the substrate, to become excited and emit a spectral range that is dependent on the species and number of species of water-soluble nanocrystals used to label the substrate. Thus, another function of the beam splitter is to then direct light emitted from the spectral range may be transmitted to the G coded photo-detector, and a beam of a selected spectral range may be transmitted to the B coded photodetector. Each of the plurality of beams may comprise a spectral range that may be the same or may differ (as compared to the spectral range of one or more of the other beams of the plurality), as may be appropriate for the photodetector to which it is transmitted. In another variation of this embodiment, the beam splitter is selected and operatively positioned to transmit emitted light to the detector means comprising only a portion of the spectral range of from about 415 nm to about 800 nm. For example, the beam splitter may be chosen to transmit emitted light in the spectral range of from about 415 nm to about 550 nm, which would correspond to detection of colors ranging from blue to green to yellow in a multi-color fluorescence analysis. In another example, the beam splitter may be chosen to transmit emitted light in the spectral range of from about 530 nm to about 750 nm, which would correspond to detection of colors ranging from yellow to orange to red in a multicolor fluorescence analysis. The beam splitter may be chosen to transmit other spectral ranges comprising a portion of the range of from about 415 nm to about 800 nm, as will be apparent to those skilled in the art based on the descriptions herein. The invention may be practiced using a beam splitter that transmits a preferred spectral range comprising a portion (ranging over a spectral band of about 100 nm or greater) of the range of from about 415 nm to about 800 nm to the exclusion of spectral ranges other than the preferred spectral range. As illustrated in FIG. 7, fluorescence cube 10 according to this embodiment may further comprise a barrier filter 34 operatively positioned between beam splitter 25 and detector means 32. Preferably, the barrier filter blocks out light of less than about 400 nm from reaching the detector means; and also preferred, the barrier filter blocks out light of less than about 420 nm from reaching the detector means.

EXAMPLE 1

This example illustrates fluorescent analysis in which the fluorescence cube is used in a detection system. In this illustration, produced were water-soluble nanocrystals comprising a core, a shell, a capping compound comprising the formula $HS(CH_2)_nX$ wherein X is a carboxylate, a diaminocarboxylic acid which is operably linked to the capping compound, and an affinity ligand (comprising lectin wheat germ agglutinin, "WGA") which is operably linked to the diaminocarboxylic acid (WGA at a concentration approximated to be about one nanocrystal per lectin molecule). The functionalized nanocrystals were of a monodisperse size for emitting a yellow fluorescence in imaging a substrate. The functionalized nanocrystals were used to image liver tissue morphology; and in particular, sinusoidal liver endothelium and its distribution in the liver. The target substrates in the sinusoidal liver endothelium are sinusoidal liver endothelial cells, termed LEC-1 cells, which preferentially express N-acetyl glucosamine in higher concentrations than most other liver endothelial cell populations, and which are adjacent to portal veins ("periportal"). WGA, having binding specificity for N-acetyl glucosamine, was used as the affinity ligand of the functionalized nanocrystals to target the substrate, LEC-1 expressing N-acetyl glucosamine, in the living tissue to be imaged.

In continuing with this illustration, a BALB/c mouse was anesthetized and then placed in a supine position. Heparin (0.1 ml) was administered, and after a ten minute delay, the abdomen was surgically opened. The portal vein was exposed by upward traction on the underside of the liver and downward counter action on the duodenum, and inserted therein was a plastic tube connected to a syringe. Via the syringe, phosphate buffered saline (PBS) was perfused through the liver at a rate of about 0.1 ml per second, for a total of 5–10 ml of perfusion. The PBS and displaced blood was allowed to exit through a severed vein. An effective amount of the functionalized nanocrystals was diluted in 1 ml of PBS, in a final concentration of $8.1 \times 10^{-7}$ M (WGA concentration approximated to be about 29 µg/ml) and the mixture was then perfused at 0.1 ml/second. The mixture was allowed to remain in the liver for about 5 to 10 minutes, and then the liver was perfused again with between 5 to 10 ml of PBS. This perfusion was intended to remove any unbound or non-specifically functionalized nanocrystals from the liver. The liver was removed, and then processed. In this illustration, processing of the tissue comprised freezing the liver in a cryostat (−20° C.), and cutting of frozen sections (5–10 µ). Frozen sections were placed on slides within the cryostat, and air-dried at room temperature; some slides were fixed with alcohol; and all slides were treated with mounting fluid and cover-slipped. Various mounting fluids were used; e.g., gel mount, crystal mount, or cytoseal, for microscopy. A few of the sections, before cover-slipping, were also processed by counter-staining with DAPPI for visualization of the nuclei of hepatocytes and endothelial cells (e.g., to give a background which enhanced the contrast and details, such as positioning, of the fluorescing cells of the tissue relative to other cells in the liver).

Figure 2:
FIG. 2 is a black and white photographic representation showing liver endothelium labeled with water-soluble nanocrystals, as imaged in color using a fluorescence cube according to the present invention.

The sections were imaged by a detection system comprising a fluorescence microscope operatively coupled to a fluorescence cube according to the present invention. In addition to a housing, the fluorescence cube was comprised of an exciter filter, and a dichroic mirror designed so that transmitted to the detector means (eyepiece, or attached CCD camera) was emitted light of a spectral range of from about 530 nm to about 700 nm. Using this detection system comprising the fluorescence cube and the fluorescence microscope, a true color image of liver endothelium, and particularly of the distribution of LEC-1 cells labeled with the functionalized nanocrystals, was obtained (FIG. 2, black and white image shown). As can be seen in FIG. 2, the acquired fluorescence spectral range is used to image the LEC-1 cells that surround the portal domain sinusoids of the imaged liver. No staining occurs outside of this region. This result is consistent with the known lectin-binding patterns of the liver sinusoids. The detection system may further comprise available computer hardware or software or digital camera (CCD camera) for processing and printing a true color image of the tissue.

EXAMPLE 2

Figures 3A, 3B, 3C, 3D:
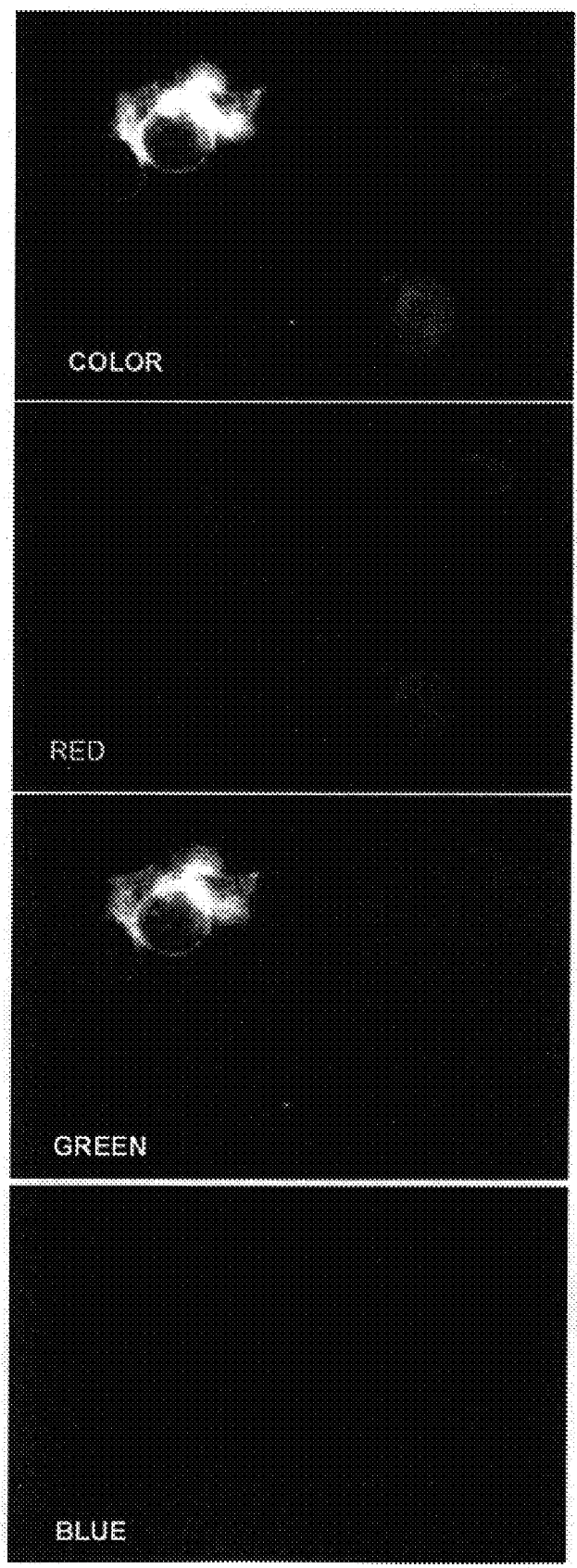
FIG. 3A is a representative image of all colors from the labeled cells.
FIG. 3B is a representative image of red color from the labeled cells.
FIG. 3C is a representative image of green color from the labeled cells.
FIG. 3D is a representative image of blue color from the labeled cells.

In an illustration of using the fluorescence cube according to the present invention to acquire fluorescence spectra in multicolor fluorescence analysis, two different species of water-soluble nanocrystals were produced. One species of water-soluble nanocrystals was of a monodisperse size for emitting a yellow-green fluorescence, and contained WGA as affinity ligand which is operably linked to diaminocarboxylic acid (WGA at a concentration approximated to be about one nanocrystal per lectin molecule). Another species of water-soluble nanocrystals was of a monodisperse size for emitting a red fluorescence, and contained Peanut agglutinin (PNA) as the affinity ligand which is operably linked to the diaminocarboxylic acid (PNA at a concentration approximated to be about one nanocrystal per lectin molecule). The two species of functionalized nanocrystals were used to image a combination of two cell types. The murine cells subjected to labeling and imaging comprised LEC-1 cells (expressing N-acetyl glucosamine, and minimal galactosyl ($\beta$1,3) N-acetyl galactosamine), and B16F10 melanoma cells (which express galactosyl ($\beta$1,3) N-acetyl galactosamine and minimal N-acetyl glucosamine). Briefly, 1 million of each cell type was mixed together with 2 ml of buffer (PBS) in forming the cell mixture. The cell mixture was then incubated with effective amounts of the two species of functionalized nanocrystals for 20 minutes at room temperature with gentle agitation. The cell mixture was then centrifuged; the cells were washed three times with buffer to remove unbound and non-specifically bound detector molecules; and then the resultant labeled cells were resuspended in 400 $\mu$l of buffer. A sample of 20 $\mu$l of the labeled cells was dropped onto a glass slide; and the slide was coverslipped, and sealed with wax. The coverslipped sample was imaged by a detection system comprising a fluorescence microscope operatively coupled to a fluorescence cube according to the present invention. In addition to a housing, the fluorescence cube was comprised of an exciter filter, and a dichroic mirror designed so that transmitted to the detector means (eyepiece, or attached CCD camera) was emitted light of a spectral range of from about 415 nm to about 800 nm. Using this detection system comprising the fluorescence cube operatively coupled to a fluorescence microscope, a true color image of the labeled cells was obtained. More particularly, the resultant image is shown in FIG. 3. FIG. 3A is a black and white representation of the fluorescing cells (comprising an image in both colors) imaged using the detection system. FIG. 3B is a black and white representation of only labeled cells fluorescing red, as selectively imaged from FIG. 3A using software and a computer to selectively view a certain color. The cells prominently stained red were confirmed by morphology to be B16F10 melanoma cells. FIG. 3C is a black and white representation of only labeled cells fluorescing yellow-green ("green"; FIG. 3C), as selectively imaged from FIG. 3A. The cells prominently stained green were confirmed by morphology to be LEC-1 cells. FIG. 3D is a black and white representation, as selectively imaged from FIG. 3A, showing that none of the labeled cells are fluorescing blue.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed:

1. A fluorescence cube comprising:
    (a) a housing;
    (b) an exciter filter which allows passage of an incident light comprising a spectral range of from about 200 nanometers to about 400 nanometers; and
    (c) a dichroic mirror, wherein the dichroic mirror reflects the incident light in a desired direction, wherein the dichroic mirror transmits a light comprising an emitted light in a desired direction, and wherein the transmitted light comprises a spectral range of from about 415 nanometers to about 800 nanometers.

2. The fluorescence cube according to claim 1, wherein the incident light comprises a spectral range of from about 310 nanometers to about 400 nanometers with a maximum transmission peak from about 360 nanometers to about 365 nanometers.

3. The fluorescence cube according to claim 1, wherein the incident light comprises a spectral range of from about 355 nanometers to about 375 nanometers with a maximum transmission peak at about 365 nanometers.

4. The fluorescence cube according to claim 1, wherein the transmitted light comprises a spectral range of from about 420 nanometers to about 750 nanometers.

5. The fluorescence cube according to claim 1, wherein the transmitted light comprises a spectral range of from about 415 nanometers to about 550 nanometers.

6. The fluorescence cube according to claim 1, wherein the transmitted light comprises a spectral range of from about 530 nanometers to about 750 nanometers.

7. The fluorescence cube according to claim 1, wherein the desired direction in which is transmitted the emitted light is to a detector means.

8. The fluorescence cube according to claim 7, wherein emitted light in a spectral range of less than 400 nanometers is reflected away from the detector means.

9. The fluorescence cube according to claim 7, wherein emitted light in a spectral range of less than 400 nanometers and emitted light in a spectral range of greater than 800 nanometers are reflected away from the detector means.

10. The fluorescence cube according to claim 1, further comprising a barrier filter operatively positioned between the dichroic mirror and a detector means.

11. The fluorescence cube according to claim 10, wherein the barrier filter blocks out light of a spectral range of less than 400 nanometers from reaching the detector means.

12. The fluorescence cube according to claim 10, wherein the barrier filter blocks out light of a spectral range of less than 420 nanometers from reaching the detector means.

13. A method of using the fluorescence cube according to claim 1 for acquiring multicolor fluorescence images, the method comprising:
    (a) fluorescence labeling of a substrate with more than one species of water-soluble nanocrystals; and
    (b) imaging the labeled substrate with a detection system comprising the fluorescence cube by exposing the labeled substrate to an incident light comprising an excitation spectral range, and detecting a transmitted light comprising an emission spectral range.

14. A method of using the fluorescence cube according to claim 10 for acquiring multicolor fluorescence images, the method comprising:
(a) fluorescence labeling of a substrate with more than one species of water-soluble nanocrystals; and
(b) imaging the labeled substrate with a detection system comprising the fluorescence cube by exposing the labeled substrate to an incident light comprising an excitation spectral range, and detecting a transmitted light comprising an emission spectral range.

15. A fluorescence cube comprising:
(a) a housing;
(b) an exciter filter which allows passage of an incident light comprising a spectral range of from about 200 nanometers to about 400 nanometers; and
(c) a beam splitter, wherein the beam splitter directs the incident light in a desired direction, wherein the beam splitter transmits a light comprising an emitted light in a desired direction, and wherein the transmitted light comprises a spectral range of from about 415 nanometers to about 800 nanometers.

16. The fluorescence cube according to claim 15, wherein the incident light comprises a spectral range of from about 310 nanometers to about 400 nanometers with a maximum transmission peak from about 360 nanometers to about 365 nanometers.

17. The fluorescence cube according to claim 15, wherein the incident light comprises a spectral range of from about 355 nanometers to about 375 nanometers with a maximum transmission peak at about 365 nanometers.

18. The fluorescence cube according to claim 15, wherein the transmitted light comprises a spectral range of from about 420 nanometers to about 750 nanometers.

19. The fluorescence cube according to claim 15, wherein the transmitted light comprises a spectral range of from about 415 nanometers to about 550 nanometers.

20. The fluorescence cube according to claim 15, wherein the transmitted light comprises a spectral range of from about 530 nanometers to about 750 nanometers.

21. The fluorescence cube according to claim 15, wherein the desired direction in which is transmitted the emitted light is to a detector means.

22. The fluorescence cube according to claim 21, wherein emitted light in a spectral range of less than 400 nanometers is reflected away from the detector means.

23. The fluorescence cube according to claim 21, wherein emitted light in a spectral range of less than 400 nanometers and emitted light in a spectral range of greater than 800 nanometers are reflected away from the detector means.

24. The fluorescence cube according to claim 15, further comprising a barrier filter operatively positioned between the beam splitter and a detector means.

25. The fluorescence cube according to claim 24, wherein the barrier filter blocks out light of a spectral range of less than 400 nanometers from reaching the detector means.

26. The fluorescence cube according to claim 24, wherein the barrier filter blocks out light of a spectral range of less than 420 nanometers from reaching the detector means.

27. The fluorescence cube according to claim 15, wherein the beam splitter is selected from the group consisting of a prism beam splitter and a plate beam splitter.

28. The fluorescence cube according to claim 15, wherein the beam splitter comprises a prism beam splitter, and the emitted light transmitted by the beam splitter to a detector means comprises a plurality of beams.

29. A method of using the fluorescence cube according to claim 15 for acquiring multicolor fluorescence images, the method comprising:
(a) fluorescence labeling of a substrate with more than one species of water-soluble nanocrystals; and
(b) imaging the labeled substrate with a detection system comprising the fluorescence cube by exposing the labeled substrate to an incident light comprising an excitation spectral range, and detecting a transmitted light comprising an emission spectral range.

30. A method of using the fluorescence cube according to claim 24 for acquiring multicolor fluorescence images, the method comprising:
(a) fluorescence labeling of a substrate with more than one species of water-soluble nanocrystals; and
(b) imaging the labeled substrate with a detection system comprising the fluorescence cube by exposing the labeled substrate to an incident light comprising an excitation spectral range, and detecting a transmitted light comprising an emission spectral range.

* * * * *